United States Patent [19]

Sucrow et al.

[11] 4,434,073
[45] Feb. 28, 1984

[54] PERHYDROPHENANTHRENE DERIVATIVES, THEIR PREPARATION, AND THEIR USE IN LIQUID-CRYSTALLINE DIELECTRICS AND ELECTRO-OPTICAL DISPLAY ELEMENTS

[75] Inventors: Wolfgang Sucrow, Paderborn; Hans-Rüdiger Murawski, Lampertheim; Hermann Minas; Horst Stegemeyer, both of Paderborn, all of Fed. Rep. of Germany

[73] Assignee: Merck Patent Gesellschaft Mit Beschrankter Haftung, Darmstadt, Fed. Rep. of Germany

[21] Appl. No.: 447,822

[22] Filed: Dec. 8, 1982

[30] Foreign Application Priority Data

Dec. 8, 1981 [DE] Fed. Rep. of Germany ....... 3148448

[51] Int. Cl.³ .......................... C09K 3/34; G02F 1/13; C07C 13/60; C07C 23/44; C07C 43/18; C07C 69/013; C07C 121/46
[52] U.S. Cl. ........................... 252/299.62; 252/299.5; 252/299.63; 260/465 C; 350/350 R; 560/1; 570/187; 570/188; 568/665; 585/21
[58] Field of Search .............. 260/465 C; 252/299.62, 252/299.63, 299.5; 570/187, 188; 585/21; 568/665; 560/1; 350/350 R

[56] References Cited

U.S. PATENT DOCUMENTS

| | | | |
|---|---|---|---|
| 3,755,361 | 8/1973 | Shaw et al. .............................. | 560/1 |
| 3,947,375 | 3/1976 | Gray et al. ...................... | 252/299.62 |
| 3,984,419 | 10/1976 | Hauck et al. ........................ | 560/103 |
| 4,095,029 | 6/1978 | Fields ..................................... | 560/87 |
| 4,113,726 | 9/1978 | Hauck et al. ........................ | 560/103 |
| 4,130,502 | 12/1978 | Eidenschink et al. ......... | 252/299.63 |
| 4,154,697 | 5/1979 | Eidenschink et al. ......... | 252/299.63 |
| 4,324,644 | 4/1982 | Dura-Swamy ................... | 208/8 LE |
| 4,386,007 | 5/1983 | Krause et al. .................... | 252/299.62 |

FOREIGN PATENT DOCUMENTS

| | | | |
|---|---|---|---|
| 57-54130 | 3/1982 | Japan .............................. | 252/299.62 |
| 2082174 | 3/1982 | United Kingdom ........... | 252/299.62 |
| 2084576 | 4/1982 | United Kingdom ........... | 252/299.62 |
| 2090593 | 7/1982 | United Kingdom ........... | 252/299.62 |
| 2093057 | 8/1982 | United Kingdom ........... | 252/299.62 |

OTHER PUBLICATIONS

Demus, D., et al., Flüssige Kristalle in Tabellen, pp. 244–247 (1974).
Praefcke, K., et al., Chem. Zeitung, vol. 104, No. 9, pp. 269–271 (1980).

*Primary Examiner*—Teddy S. Gron
*Attorney, Agent, or Firm*—Millen & White

[57] ABSTRACT

Perhydrophenanthrene derivatives of formula I

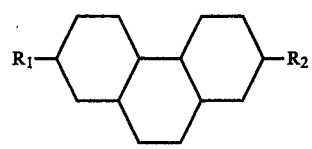

I wherein $R_1$ is alkyl of 1–10 C atoms and $R_2$ is alkyl, alkoxy or alkanoyloxy each of 1–10 C atoms, H, Br, Cl or CN, have an extremely low optical anisotropy and are particularly suitable as components of liquid-crystalline dielectrics.

15 Claims, No Drawings

PERHYDROPHENANTHRENE DERIVATIVES, THEIR PREPARATION, AND THEIR USE IN LIQUID-CRYSTALLINE DIELECTRICS AND ELECTRO-OPTICAL DISPLAY ELEMENTS

BACKGROUND OF THE INVENTION

The properties of liquid-crystalline materials whereby they significantly vary their optical properties, such as light absorption, light scattering, birefringence, reflectivity or color, under the influence of electric fields, are widely utilized for electro-optical display elements. Thus, the functioning of display elements of this type is based, for example, on the phenomena of dynamic scattering, the deformation of aligned phases, the Schadt-Helfrich effect in the twisted cell or the cholesteric-nematic phase transition.

For the industrial application of these effects in electronic components, liquid-crystalline dielectrics are required which must meet a large number of demands. Chemical resistance to moisture, air and physical influences, such as heat, radiation in the infra-red, visible and ultraviolet regions and continuous and alternating electric fields, is of particular importance. Industrially usable liquid-crystalline dielectrics are also required to have a liquid-crystalline mesophase in the temperature range from at least 0° C. to +50° C., preferably from −10° C. to 60° C., and the lowest possible viscosity at room temperature, which preferably should not exceed $50 \times 10^{-3}$ Pa.s. Finally, they must not have any characteristic absorption in the visible region, i.e., they must be colorless.

A number of liquid-crystalline compounds have already been disclosed, which fulfill the stability demands made on dielectrics for electronic components, and which are also colorless. However, no single compounds have yet been disclosed which fulfill all the requirements in respect of the range of temperature of the liquid-crystalline mesophase, the dielectric anisotropy, the optical anisotropy, the viscosity, the specific resistance and the shape of the electrooptical characteristic curve.

For this reason, mixtures are employed. Their compositions are adapted to the requirements in each case. In order to vary the properties of the mixtures, as many different substances as possible are required, if possible from different classes of substances. This provides sufficient scope in which to change the properties of the mixtures of substances. For this reason, there is a constant search for new liquid-crystals with advantageous properties.

SUMMARY OF THE INVENTION

Accordingly, it is an object of this invention to prepare liquid-crystalline dielectrics which have a nematic phase in the required temperature range and which enable sufficiently short switching times in liquid-crystal cells at room temperature.

Upon further study of the specification and appended claims, further objects and advantages of this invention will become apparent to those skilled in the art.

These objects have been attained by providing perhydrophenanthrene derivatives of formula I

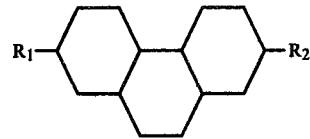

wherein $R_1$ is alkyl of 1-10 C atoms and $R_2$ is alkyl, alkoxy or alkanoyloxy each of 1-10 C atoms, H, Br, Cl or CN.

These compounds are valuable components of liquid-crystalline dielectrics. In particular, they have favorable clear points in the temperature range of about 50° to 120°, and at the same time comparatively low melting points and an extremely low optical anisotropy in the region of about 0.02 to 0.06. Thus, they are particularly suitable as components of liquid-crystalline dielectrics for electro-optical display elements of the type disclosed in German Patent Application No. 3,022,818, corresponding to U.S. application Ser. No. 273,271 of June 15, 1981, now U.S. Pat. No. 4,398,803 whose disclosures are incorporated by reference herein, and also for improving the contrast in guest-host liquid-crystal display elements. Furthermore, they have a negative anisotropy of diamagnetic susceptibility, which makes them suitable for use in electro-optical modulators according to European Patent Specification No. 1,745, whose disclosure is incorporated by reference herein.

Thus, this invention relates to perhydrophenanthrene derivatives of formula I and their use as components of liquid-crystalline dielectrics. The invention further relates to liquid-crystalline dielectrics containing at least one perhydrophenanthrene derivative of formula I and electro-optical display elements based on a liquid-crystal cell which contains a liquid-crystalline dielectric of this type.

DETAILED DISCUSSION

In the compounds of formula I, $R_1$ is an alkyl group having 1-10 C atoms, and thus is methyl, ethyl, propyl, butyl, pentyl, hexyl, heptyl, octyl, nonyl or decyl. In principle, those groups which contain 3 or more C atoms can be straight-chain or branched; however, when an alkyl group $R_1$ has a branched chain, as a rule it contains not more than one chain branching. In this context, of the branched alkyl groups, those are preferred in which a methyl or ethyl group is present in the 2- or 3-position on a relatively long carbon chain, for example, 2- or 3-methylbutyl, 2- or 3-methylpentyl or 2- or 3-ethylhexyl. When the radical $R_2$ in the compounds of formula I also contains a carbon chain, and thus is alkyl, alkoxy, or alkanoyloxy, usually only one of the two radicals, at the most, contains a carbon chain which is branched once. When $R_2$ is alkyl, alkoxy or alkanoyloxy, $R_1$ and $R_2$ together can contain 2 to 20 C atoms. In this context, however, those perhydrophenanthrene derivatives of formula I are preferred in which $R_1$ and $R_2$ together contain 3-16, preferably 4-14, C atoms, In the compound of formula I wherein $R_2$ is hydrogen, Br, Cl or CN, $R_1$ preferably contains at least 2, but, in particular, 3 or more C atoms.

This invention further relates to a process for the preparation of the perhydrophenanthrene derivatives of formula I, comprising reducing a ketone of formula II

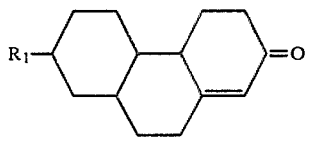

(optionally stepwise) to produce a compound of formula III

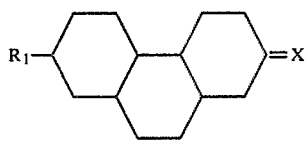

wherein X is O or (H,OH); and converting III (X=O), by reaction with a compound of the formula R′$_2$-M, wherein R′$_2$ is alkyl of 1–10 C atoms, M is Li or MgHal and Hal is chlorine, bromine or iodine, hydrolysis, splitting off water and hydrogenation, into a compound of formula I, wherein R$_2$ is alkyl of 1–10 C atoms; or converting III (X=H,OH), by splitting off water and hydrogenation, into a compound of formula I, in which R$_2$ is H; converting III (X=H,OH), by etherification or esterification, into a compound of formula I, in which R$_2$ is alkoxy or alkanoyloxy, each of 1–10 C atoms; or converting III (X=H,OH), by reaction with a chlorinating agent or brominating agent for hydroxy compounds, into a compound of formula I, in which R$_2$ is Cl or Br; and, if appropriate, converting a compound of this type or a sulfonate of a compound of formula III (X=H,OH), by reaction with a metal cyanide, into a compound of formula I in which R$_2$ is CN.

Furthermore, the compounds of formula I can be prepared by these methods known per se or other methods known per se; all are described in the literature (for example in the standard works, such as Houben-Weyl, Methoden der Organischen Chemie (Methods of Organic Chemistry), Georg-Thieme Verlag, Stuttgart; Organic Reactions, John Wiley & Sons, Inc., New York, whose disclosure is incorporated by reference herein), namely under reaction conditions which are known and suitable for the reactions mentioned. For this purpose, use can also be made of variants which are known per se but which are not mentioned here in more detail.

The starting materials can, if desired, also be formed in situ, in such a manner that they are not isolated from the reaction mixture but are immediately reacted further to give the compounds of formula I.

The starting materials of formulae II and III are new. They can also be fully conventionally obtained, for example, as follows (see the above-cited references for example):

A cyclohexanone of formula IV

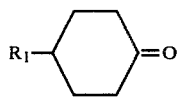

is initially condensed in the presence of a base, for example morpholine, with methyl vinyl ketone to give the diketone of formula V

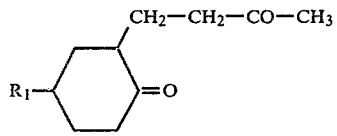

This is then cyclized in the presence of an alkali metal hydroxide, for example NaOH, to give the octahydronaphthalene derivative of formula VI

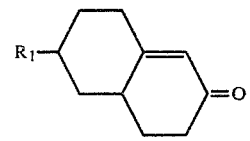

A methyl ethyl ketone derivative of formula VII

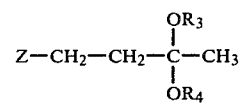

is added onto VI in the presence of a strong base in a polar aprotic solvent, for example sodium dimethyl sulfoxide in dimethyl sulfoxide.

In formula VII, Z is chlorine or bromine and R$_3$ and R$_4$ are alkyl of 1–4 C atoms or together are alkylene of 2-C atoms.

The double bond in the compound of formula VIII obtained thereby is initially selectively reduced by a Birch reduction and, after splitting off the protective group by treatment with an alkali metal hydroxide, the reduction product is cyclized in an anhydrous organic solvent to give the ketone II.

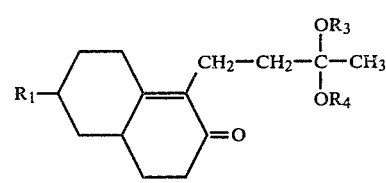

The reduction of the unsaturated ketone II to give the saturated ketone III (X=O) or to give the alcohol III (X=H,OH) is preferably carried out in the fully conventional manner of a Birch reduction with lithium in liquid ammonia. The saturated ketone III (X=O) can be converted, by reaction with an organometallic compound of the formula R′$_2$-M, preferably in an ether, such as diethyl ether, tetrahydrofuran (THF) or dioxane, and subsequent hydrolysis, splitting off of water by acid treatment, for example with p-toluenesulfonic acid, and subsequent hydrogenation, into a compound of formula I in which R$_2$ is alkyl.

The perhydrophenanthrene derivatives of formula I wherein R$_2$ is H can be obtained either by subjecting the ketone III (X=O) to a Wolff-Kishner reduction, or by splitting off water from the alcohol III (X=H,OH) in the presence of an acid, followed by hydrogenation of the unsaturated compound produced. Compounds of formula I wherein R$_2$ is an alkoxy group can be prepared from the alcohol III (X=H,OH) by etherification, for example by reaction with an alkyl halide in the presence of a base. The perhydrophenanthrene derivatives of formula I in which $R_2$ is an alkanoyloxy group can be prepared from the alcohol III (X=H,OH) by esterification with a carboxylic acid $R''_2$-COOH, wherein $R''_2$ is an alkyl group having 1-9 carbon atoms, or a reactive derivative of a carboxylic acid of this type, for example a carbonyl chloride or carboxylic anhydride.

The compounds of formula I, in which $R_2$ is Cl or Br, can be obtained from the alcohol III (X=H,OH) by treatment with a chlorinating or brominating agent, for example thionyl chloride or bromide.

The preparation of the perhydrophenanthrene derivatives of formula I wherein $R_2$ is CN can be carried out by reactions of the chlorine or bromine compounds with a cyanide, for example potassium cyanide or silver cyanide. Reactive esters of the alcohol III (X=H,OH), for example the tosylate, can also be used instead of the chlorine or bromine compounds I ($R_2$=Cl, Br).

The compounds of formula I have several centers of asymmetry. Thus, on preparation, they can be obtained as racemates or, if optically active starting materials are used, also in an optically active form. If mixtures of racemates are produced, the individual racemates can be isolated in a pure form from these, for example by recrystallization of the racemates themselves or of their diastereomeric derivatives from inert solvents.

However, the synthesis is preferably carried out in such a manner that the preferred racemates of the configuration Ia are formed either predominantly or exclusively:

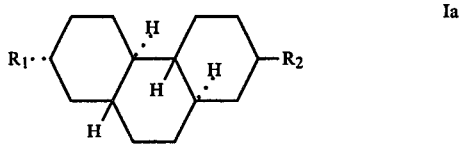

Ia wherein the two substituents $R_1$ and $R_2$ are equatorial. However, all optical isomers, mixtures thereof and configurations are included in this invention.

Racemates obtained can be separated, if desired, into their optical antipodes either mechanically or chemically by methods known per se.

The dielectrics according to this invention comprise 2 to 15, preferably 3 to 12, components, including at least one perhydrophenanthrene derivative of formula I. The other constituents are selected from the nematic or nematogenic substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines or cyclohexylpyrimidines, phenyldioxanes or cyclohexyldioxanes, stilbenes which may be halogenated, benzyl phenyl ethers, tolanes and substituted cinnamic acids. The most important compounds which can be used as constituents of liquid-crystalline dielectrics of this type can be characterized by formula IX,

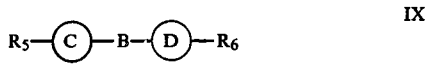

IX wherein the C and D systems are each independently a carbocyclic or heterocyclic ring system from the group comprising 1,4-disubstituted benzene and cyclohexane rings, 4,4'-disubstituted biphenyl, phenyl cyclohexane and cyclohexyl cyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline; B is

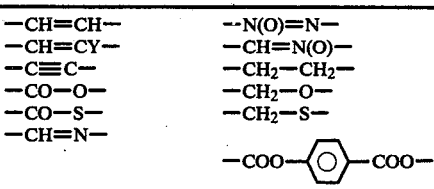

or a C—C single bond; Y is halogen, preferably chlorine, or —CN; and $R_5$ and $R_6$ are alkyl, alkoxy, alkanoyloxy or alkoxycarbonyloxy each of up to 18, preferably up to 8, carbon atoms, or one of these radicals is also —CN, —NC, —NO$_2$, —CF$_3$, F, CL or Br. In most of these compounds, $R_5$ and $R_6$ are different from one another, one of these radicals beings an alkyl group or an alkoxy group in most cases. Other variants of the envisaged substituents, however, are also common. Many such substances, or also mixtures thereof, are commercially available.

The dielectrics according to this invention contain, as a rule, at least 30, preferably 50–99, in particular 60–98, percent by weight of the compounds of the formulae I and IX. Of this, preferably at least 5 percent by weight, and in most cases even 10–40 percent by weight, is provided by one or more compounds of formula I. However, the invention also comprises those liquid-crystalline dielectrics to which only less than 5 percent by weight, for example 0.1 to 3 percent by weight, of one or more compounds of formula I have been added, for example for doping purposes. On the other hand, the compounds of formula I can account for up to 60 percent by weight of the dielectrics according to this invention. Preferably, the liquid-crystalline dielectrics of this invention contain 10 to 30 percent by weight of one or more compounds of formula I.

The preparation of the dielectrics according to this invention is carried out in a manner conventional per se. As a rule, the desired amount of the components used in a smaller quantity is dissolved in the component representing the main constituent, advantageously at an elevated temperature. If a temperature above the clear point of the main constituent is chosen for this, the completeness of the solution process can be observed with particular ease.

The liquid-crystalline dielectrics according to this invention can be modified by suitable additives in such a way that they can be used in all hitherto disclosed types of liquid crystal display elements. Additives of this type are known to those skilled in the art and are extensively described in the relevent literature. For example, it is possible to add dichroic dyes or substances which are intended to modify the dielectric anisotropy, the viscosity, the conductivity and/or the orientation of the nematic phases. Substances of these types are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point of a liquid-crystalline substance in degrees centigrade; boiling points are marked b.p.

"Normal work-up" indicates: water is added, if necessary; the mixture is extracted with ether, separated, and the organic phase is dried over sodium sulfate, filtered, evaporated and purified, where appropriate, by column chromatography (the absorbent and the eluant are indicated in brackets).

In the following examples, 4a$\beta$, 4b$\alpha$, 8a$\beta$, 10a$\alpha$-perhydrophenanthrene is abbreviated as "perhydrophenanthrene."

PREPARATION EXAMPLES

EXAMPLE 1

A solution of 2.9 g of 7$\alpha$-hexyl-2$\beta$-perhydrophenanthrenol (m.p. 126°; obtained by reaction of 4-hexylcyclohexanone with morpholine to give 4-n-hexyl-1-morpholino-1-cyclohexene (b.p. 143°/0.01 Torr), reaction with methyl vinyl ketone to give 4-hexyl-2-(3-oxobutyl)cyclohexanone (b.p. 158°/0.01 Torr), cyclization to give 6$\alpha$-hexyl-2,3,4,4a$\beta$,5,6,7,8-octahydro-2-naphthalenone (b.p. 136°–140°/1.5 Torr), reaction with 1-bromo-3,3-ethylenedioxybutane to give 1-(3,3-ethylenedioxybutyl)-6$\alpha$-hexyl-2,3,4,4a$\beta$,5,6-7,8-octahydro-2-naphthalenone, reduction with Li/NH$_3$ to give 1$\alpha$-(3,3-ethylenedioxybutyl)-6$\alpha$-hexyl-4a$\beta$,8a$\alpha$-decahydro-2-naphthalenone, ketal cleavage and cyclization to give 7$\alpha$-hexyl-4a$\beta$,4b$\alpha$,8a$\beta$-dodecahydro-2-phenanthrenone (m.p. 77°), Birch reduction to give 7$\alpha$-hexylperhydro-2-phenanthrenone (m.p. 49°) and further Birch reduction after the addition of methanol) and 0.3 g of p-toluenesulfonic acid in 30 ml of toluene was boiled under a water separator for 2 hours. The mixture was allowed to cool down, filtered through Al$_2$O$_3$ and evaporated. The residue was hydrogenated in 30 ml of THF on 0.5 g of 5% Pd-C at 60° and 6 bar until no further change. After filtration and evaporation, 7$\alpha$-hexylperhydrophenanthrene was obtained.

EXAMPLES 2 to 10

In analogy to Example 1, the following compounds are obtained from the corresponding 4-R$_1$-cyclohexanones via the corresponding 7$\alpha$-R$_1$-perhydro-2-phenanthrenones and 7$\alpha$-R$_1$-perhydro-2-phenanthrenols:

2. 7$\alpha$-Methylperhydrophenanthrene.
3. 7$\alpha$-Ethylperhydrophenanthrene.
4. 7$\alpha$-Propylperhydrophenanthrene.
5. 7$\alpha$-Butylperhydrophenanthrene.
6. 7$\alpha$-Pentylperhydrophenanthrene.
7. 7$\alpha$-Heptylperhydrophenanthrene.
8. 7$\alpha$-Octylperhydrophenanthrene.
9. 7$\alpha$-Nonylperhydrophenanthrene.
10. 7$\alpha$-Decylperhydrophenanthrene.

EXAMPLE 11

A solution of 145 g of 7$\alpha$-hexylperhydro-2-phenanthrenone in 200 ml of ether was added dropwise to a Grignard solution prepared from 85 g of hexyl bromide and 13 g of magnesium in 400 ml of ether, with stirring and cooling. After boiling for one hour, the mixture was poured onto dilute hydrochloric acid/ice and extracted several times with ether; the extracts were washed to neutrality, dried over sodium sulfate and evaporated. The crude mixture of 2$\alpha$-7$\alpha$-dihexyl-2$\beta$-perhydrophenanthrenol 2$\beta$,7$\alpha$-dihexyl-2$\alpha$-perhydrophenanthrenol obtained was dissolved in 400 ml of toluene. After adding 10 g of p-toluenesulfonic acid, the mixture was boiled for 3 hours under a water separator, allowed to cool, filtered through Al$_2$O$_3$ and evaporated. The crude mixture of 2,7$\alpha$-dihexyldodecahydrophenanthrenes was hydrogenated in 1 l of tetrahydrofuran with 50 g of 5% Pd-C at 60° and 6 bar until no further change. After filtration and evaporation, a mixture of 2$\alpha$,7$\alpha$- and 2$\beta$,7$\alpha$-dihexylperhydrophenanthrene was obtained, which can be separated by HPLC.

EXAMPLES 12 to 20

In analogy to Example 11, the following compounds are obtained from the corresponding 7$\alpha$-R$_1$-perhydro-2-phenanthrenones:

12. 2$\alpha$,7$\alpha$- and 2$\beta$,7$\alpha$-Dimethylperhydrophenanthrene.
13. 2$\alpha$,7$\alpha$- and 2$\beta$,7$\alpha$-Diethylperhydrophenanthrene.
14. 2$\alpha$,7$\alpha$- and 2$\beta$,7$\alpha$-Dipropylperhydrophenanthrene.
15. 2$\alpha$,7$\alpha$- and 2$\beta$,7$\alpha$-Dibutylperhydrophenanthrene.
16. 2$\alpha$,7$\alpha$- and 2$\beta$,7$\alpha$-Dipentylperhydrophenanthrene.
17. 2$\alpha$,7$\alpha$- and 2$\beta$,7$\alpha$-Diheptylperhydrophenanthrene.
18. 2$\alpha$,7$\alpha$- and 2$\beta$,7$\alpha$-Dioctylperhydrophenanthrene.
19. 2$\alpha$,7$\alpha$- and 2$\beta$,7$\alpha$-Dinonylperhydrophenanthrene.
20. 2$\alpha$,7$\alpha$- and 2$\beta$,7$\alpha$-Didecylperhydrophenanthrene.

EXAMPLE 21

30 mg of a 55% NaH dispersion was added to a solution of 150 mg of 7$\alpha$-hexyl-2$\beta$-perhydrophenanthrenol in 25 ml of THF and the mixture was stirred for one hour under N$_2$. Then a solution of 100 mg of n-bromopentane in 5 ml of THF was added and the mixture was boiled overnight with stirring. After cooling down, the precipitated salts were removed by filtration, the filtrate was evaporated and the residue was chromatographed (silica gel 60; petroleum ether:ether=95:5). 7$\alpha$-hexyl-2$\beta$-pentyloxyperhydrophenanthrene was obtained, m.p. 55°, c.p. 64° (from methanol).

EXAMPLES 22 to 50

In analogy to Example 21, the following compounds are obtained by etherification:

22. 7$\alpha$-Ethyl-2$\beta$-propyloxyperhydrophenanthrene.
23. 2$\beta$-Butyloxy-7$\alpha$-ethylperhydrophenanthrene.
24. 7$\alpha$-Ethyl-2$\beta$-pentyloxyperhydrophenanthrene.
25. 7$\alpha$-Ethyl-2$\beta$-hexyloxyperhydrophenanthrene.
26. 7$\alpha$-Ethyl-2$\beta$-heptyloxyperhydrophenanthrene.
27. 7$\alpha$-Propyl-2$\beta$-propyloxyperhydrophenanthrene.
28. 2$\beta$-Butyloxy-7$\alpha$-propylperhydrophenanthrene.
29. 2$\beta$-Pentyloxy-7$\alpha$-propylperhydrophenanthrene.
30. 2$\beta$-Hexyloxy-7$\alpha$-propylperhydrophenanthrene.
31. 2$\beta$-Heptyloxy-7$\alpha$-propylperhydrophenanthrene.
32. 7$\alpha$-Butyl-2$\beta$-propyloxyperhydrophenanthrene.
33. 7$\alpha$-Butyl-2$\beta$-butyloxyperhydrophenanthrene.
34. 7$\alpha$-Butyl-2$\beta$-pentyloxyperhydrophenanthrene.

35. 7α-Butyl-2β-hexyloxyperhydrophenanthrene.
36. 7α-Butyl-2β-heptyloxyperhydrophenanthrene.
37. 7α-Pentyl-2β-propyloxyperhydrophenanthrene.
38. 2β-Butyloxy-7α-pentylperhydrophenanthrene.
39. 7α-Pentyl-2β-pentyloxyperhydrophenanthrene.
40. 2β-Hexyloxy-7α-pentylperhydrophenanthrene.
41. 2β-Heptyloxy-7α-pentylperhydrophenanthrene.
42. 7α-Hexyl-2β-propyloxyperhydrophenanthrene.
43. 2β-Butyloxy-7α-hexylperhydrophenanthrene.
44. 7α-Hexyl-2β-hexyloxyperhydrophenanthrene.
45. 7α-Hexyl-2β-heptyloxyperhydrophenanthrene.
46. 7α-Heptyl-2β-propyloxyperhydrophenanthrene.
47. 2β-Butyloxy-7α-heptylperhydrophenanthrene.
48. 7α-Heptyl-2β-pentyloxyperhydrophenanthrene.
49. 2β-Hexyloxy-7α-heptylperhydrophenanthrene.
50. 7α-Heptyl-2β-heptyloxyperhydrophenanthrene.

EXAMPLE 51

About 50 mg of hexanoyl chloride was added dropwise to a solution of 60 mg of 7α-hexyl-2β-perhydrophenanthrenol in 2 ml of pyridine and the mixture was stirred overnight, and then poured onto ice. After the usual work-up (silica gel; petroleum ether:CH₂Cl₂:ether=5.0:3.5:1.5), 2β-hexanoyloxy-7α-hexylperhydrophenanthrene was obtained, m.p. 57°, c.p. 76° (from ethanol).

EXAMPLES 52 to 103

In analogy to Example 51, the following compounds are obtained from the corresponding alcohols with the appropriate acid chlorides:

52. 2β-Acetoxy-7α-propylperhydrophenanthrene.
53. 2β-Acetoxy-7α-butylperhydrophenanthrene.
54. 2β-Acetoxy-7α-pentylperhydrophenanthrene.
55. 2β-Acetoxy-7α-hexylperhydrophenanthrene, m.p. 74°, c.p. 65° (monotropic).
56. 2β-Acetoxy-7α-heptylperhydrophenanthrene.
57. 2β-Propionyloxy-7α-propylperhydrophenanthrene.
58. 7α-Butyl-2β-propionyloxyperhydrophenanthrene.
59. 7α-Pentyl-2β-propionyloxyperhydrophenanthrene.
60. 7α-Hexyl-2β-propionyloxyperhydrophenanthrene, m.p. 73°, c.p. 85°.
61. 7α-Heptyl-2β-propionyloxyperhydrophenanthrene.
62. 2β-Butyryloxy-7α-propylperhydrophenanthrene.
63. 7α-Butyl-2β-butyryloxyperhydrophenanthrene.
64. 2β-Butyryloxy-7α-pentylperhydrophenanthrene.
65. 2β-Butyryloxy-7α-hexylperhydrophenanthrene, m.p. 53°, c.p. 82°.
66. 2β-Butyryloxy-7α-heptylperhydrophenanthrene.
67. 2β-Pentanoyloxy-7α-propylperhydrophenanthrene.
68. 7α-Butyl-2β-pentanoyloxyperhydrophenanthrene.
69. 2β-Pentanoyloxy-7α-pentylperhydrophenanthrene.
70. 7α-Hexyl-2β-pentanoyloxyperhydrophenanthrene, m.p. 57°, c.p. 76°.
71. 7α-Heptyl-2β-pentanoyloxyperhydrophenanthrene.
72. 2β-Hexanoyloxy-7α-propylperhydrophenanthrene.
73. 7α-Butyl-2β-hexanoyloxyperhydrophenanthrene, m.p. 68°, c.p. 60° (monotropic).
74. 2β-Hexanoyloxy-7α-pentylperhydrophenanthrene, m.p. 70°, c.p. 78°.
75. 7α-Heptyl-2β-hexanoyloxyperhydrophenanthrene, m.p. 66°, c.p. 80°.
76. 2β-Hexanoyloxy-7α-octylperhydrophenanthrene, m.p. 57°, c.p. 79°.
77. 2β-Hexanoyloxy-7α-nonylperhydrophenanthrene.
78. 7α-Decyl-2β-hexanoyloxyperhydrophenanthrene, m.p. 65°, c.p. 78°.
79. 2β-Heptanoyloxy-7α-propylperhydrophenanthrene.
80. 7α-Butyl-2β-heptanoyloxyperhydrophenanthrene.
81. 2β-Heptanoyloxy-7α-pentylperhydrophenanthrene.
82. 2β-Heptanoyloxy-7α-hexylperhydrophenanthrene, m.p. 59°, c.p. 73°.
83. 2β-Heptanoyloxy-7α-octylperhyrophenanthrene.
84. 2β-Octanoyloxy-7α-propylperhydrophenanthrene.
85. 7α-Butyl-2β-octanoyloxyperhydrophenanthrene.
86. 2β-Octanoyloxy-7α-pentylperhydrophenanthrene.
87. 7α-Hexyl-2β-octanoyloxyperhydrophenanthrene, m.p. 69°, c.p. 68° (monotropic).
88. 7α-Heptyl-2β-octanoyloxyperhydrophenanthrene.
89. 2β-Octanoyloxy-7α-octylperhydrophenanthrene.
90. 2β-Nonanoyloxy-7α-propylperhydrophenanthrene.
91. 7α-Butyl-2β-nonanoyloxyperhydrophenanthrene.
92. 2β-Nonanoyloxy-7α-pentylperhydrophenanthrene.
93. 7α-Hexyl-2β-nonanoyloxyperhydrophenanthrene, m.p. 68°, c.p. 72°.
94. 7α-Heptyl-2β-nonanoyloxyperhydrophenanthrene.
95. 2β-Nonanoyloxy-7α-octylperhydrophenanthrene.
96. 2β-Decanoyloxy-7α-propylperhydrophenanthrene.
97. 7α-Butyl-2β-decanoyloxyperhydrophenanthrene.
98. 2β-Decanoyloxy-7α-pentylperhydrophenanthrene.
99. 2β-Decanoyloxy-7α-hexylperhydrophenanthrene, m.p. 70°, c.p. 72°.
100. 2β-Decanoyloxy-7α-heptylperhydrophenanthrene.
101. 2β-Decanoyloxy-7α-octylperhydrophenanthrene.
102. 2β-Decanoyloxy-7α-nonylperhydrophenanthrene.
103. 2β-Decanoyloxy-7α-decylperhydrophenanthrene.

EXAMPLE 104

A solution of 1.74 g of triphenylphosphine in 5 ml of THF was added dropwise under nitrogen to a solution of 1.19 g of N-bromosuccinimide in 5 ml of THF. To this was added a solution of 7α-hexyl-2α-perhydrophenanthrenol (obtained from 7α-hexylperhydro-2-phenanthrenone and potassium tris-sec-butylborohydride in THF) in 5 ml of THF. The mixture was boiled for 4 hours, then further stirred overnight at 20° and worked up as usual. (Silica gel 60; n-hexane). 2β-bromo-7α-hexylperhydrophenanthrene was obtained, m.p. 92° (from acetone).

EXAMPLES 105 to 123

In analogy to Example 104, the following compounds are obtained from the corresponding alcohols with N-chlorosuccinimide or N-bromosuccinimide:

105. 2β-Chloro-7α-methylperhydrophenanthrene.
106. 2β-Chloro-7α-ethylperhydrophenanthrene.
107. 2β-Chloro-7α-propylperhydrophenanthrene.
108. 7α-Butyl-2β-chloroperhydrophenanthrene.
109. 2β-Chloro-7α-pentylperhydrophenanthrene.
110. 2β-Chloro-7α-hexylperhydrophenanthrene.
111. 2β-Chloro-7α-heptylperhydrophenanthrene.
112. 2β-Chloro-7α-octylperhydrophenanthrene.
113. 2β-Chloro-7α-nonylperhydrophenanthrene.
114. 2β-Chloro-7α-decylperhydrophenanthrene.
115. 2β-Bromo-7α-methylperhydrophenanthrene.
116. 2β-Bromo-7α-ethylperhydrophenanthrene.
117. 2β-Bromo-7α-propylperhydrophenanthrene.
118. 2β-Bromo-7α-butylperhydrophenanthrene.
119. 2β-Bromo-7α-pentylperhydrophenanthrene.
120. 2β-Bromo-7α-heptylperhydrophenanthrene.
121. 2β-Bromo-7α-octylperhydrophenanthrene.
122. 2β-Bromo-7α-nonylperhydrophenanthrene.
123. 2β-Bromo-7α-decylperhydrophenanthrene.

EXAMPLE 124

A solution of 410 mg of 7α-hexyl-2β-p-toluenesulfonyloxyperhydrophenanthrene (m.p. 71°) and 724 mg of sodium cyanide in 50 ml of N-methylpyrrolidone was stirred at 90° for 20 hours. After cooling down, the mixture was diluted with water and worked up as usual (silica gel 60; petroleum ether:ether=95:5). 2β-cyano-7α-hexyl-perhydrophenanthrene was obtained, m.p. 89°, c.p. 91°.

EXAMPLES 125 to 134

In analogy to Example 124, the following compounds are obtained from the corresponding chlorides, bromides or p-toluenesulfonates with NaCN:

125. 2β-Cyano-7α-methylperhydrophenanthrene.
126. 2β-Cyano-7α-ethylperhydrophenanthrene.
127. 2β-Cyano-7α-propylperhydrophenanthrene.
128. 7α-Butyl-2β-cyanoperhydrophenanthrene.
129. 2β-Cyano-7α-pentylperhydrophenanthrene.
130. 2β-Cyano-7α-hexylperhydrophenanthrene.
131. 2β-Cyano-7α-heptylperhydrophenanthrene.
132. 2β-Cyano-7α-octylperhydrophenanthrene.
133. 2β-Cyano-7α-nonylperhydrophenanthrene.
134. 2β-Cyano-7α-decylperhydrophenanthrene.

The following examples relate to mixtures of compounds of formula I with one another or with other liquid-crystalline substances which can be used as dielectrics according to the invention.

EXAMPLE A

A mixture of
18% of 7α-butyl-2β-hexanoyloxyperhydrophenanthrene,
17% of 2β-hexanoyloxy-7α-pentylperhydrophenanthrene,
23% of 2β-hexanoyloxy-7α-hexylperhydrophenanthrene,
20% of 7α-heptyl-2β-hexanoyloxyperhydrophenanthrene,
22% of 7α-decyl-2β-hexanoyloxyperhydrophenanthrene, shows the following data: m.p. 5°, c.p. 75°, viscosity 41 mm$^2$.sec$^{-1}$ at 20°, dielectric anisotropy −0.5, optical anisotropy +0.05.

EXAMPLE B

A mixture of
10% of 7α-butyl-2β-hexanoyloxyperhydrophenanthrene,
10% of 2β-hexanoyloxy-7α-pentylperhydrophenanthrene,
13% of 2β-hexanoyloxy-7α-hexylperhydrophenanthrene,
11% of 7α-heptyl-2β-hexanoyloxyperhydrophenanthrene,
25% of trans,trans-4-ethylcyclohexylcyclohexane-4'-carbonitrile,
4% of trans,trans-4-propylcyclohexylcyclohexane-4'-carbonitrile,
23% of trans,trans-4-butylcyclohexylcyclohexane-4'-carbonitrile,
4% of trans,trans-4-pentylcyclohexylcyclohexane-4'-carbonitrile shows the following data: m.p. −20°, c.p. 68°, viscosity 56 mm$^2$.sec$^{-1}$ at 20°, dielectric anisotropy +2.3, optical anisotropy +0.057.

EXAMPLE C

A mixture of
9% of 7α-butyl-2β-hexanoyloxyperhydrophenanthrene
9% of 2β-hexanoyloxy-7α-pentylperhydrophenanthrene
13% of 2β-hexanoyloxy-7α-hexylperhydrophenanthrene
11% of 7α-heptyl-2β-hexanoyloxyperhydrophenanthrene
25% of trans,trans-4-ethylcyclohexylcyclohexane-4'-carbonitrile
23% of trans,trans-4-butylcyclohexylcyclohexane-4'-carbonitrile
10% of trans-4-propylcyclohexyl trans,trans-4-butylcyclohexylcyclohexane-4'-carboxylate shows the following data: m.p. −5°, c.p. 77°, viscosity 52 mm$^2$.sec$^{-1}$, dielectric anisotropy +2, optical anisotropy +0.056.

EXAMPLE D

A mixture of
18% of 4-(trans-4-pentylcyclohexyl)benzonitrile
13% of 2β-hexanoyloxy-7α-hexylperhydrophenanthrene
11% of 7α-heptyl-2β-hexanoyloxyperhydrophenanthrene
25% of trans,trans-4-ethylcyclohexylcyclohexane-4'-carbonitrile
23% of trans,trans-4-butylcyclohexylcyclohexane-4'-carbonitrile
10% of trans-4-propylcyclohexyl trans,trans-4-butylcyclohexylcyclohexane-4'-carboxylate shows the following data: m.p. −6°, c.p. 74°, viscosity 47 mm$^2$.sec$^{-1}$, dielectric anisotropy +3.8, optical anisotropy +0.07.

The preceding examples can be repeated with similar success by substituting the generically or specifically described reactants and/or operating conditions of this invention for those used in the preceding examples.

From the foregoing description, one skilled in the art can easily ascertain the essential characteristics of this

What is claimed is:

1. A perhydrophenanthrene of the formula

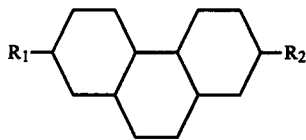

wherein $R_1$ is alkyl of 1–10 C atoms and $R_2$ is alkyl, alkoxy or alkanoyloxy each of 1–10 C atoms, H, Br, Cl or CN.

2. A perhydrophenanthrene of claim 1, wherein $R_2$ is alkyl, alkoxy or alkanoyloxy and $R_1$ and $R_2$ together contain 4–14 C atoms.

3. A perhydrophenanthrene of claim 1, wherein $R_2$ is alkyl.

4. A perhydrophenanthrene of claim 1, wherein $R_2$ is alkoxy.

5. A perhydrophenanthrene of claim 1, wherein $R_2$ is alkanoyloxy.

6. A perhydrophenanthrene of claim 1, wherein $R_2$ is straight-chain alkyl.

7. A perhydrophenanthrene of claim 1, wherein $R_2$ is straight-chain alkoxy.

8. A perhydrophenanthrene of claim 1, wherein $R_2$ is straight-chain alkanoyloxy.

9. A perhydrophenanthrene of claim 1, wherein $R_2$ is H and $R_1$ has 3 or more C atoms.

10. A perhydrophenanthrene of claim 1, wherein $R_2$ is Br and $R_1$ has 3 or more C atoms.

11. A perhydrophenanthrene of claim 1, wherein $R_2$ is Cl and $R_1$ has 3 or more C atoms.

12. A perhydrophenanthrene of claim 1, wherein $R_2$ is CN and $R_1$ has 3 or more C atoms.

13. A liquid-crystalline dielectric useful for electro-optical display elements, comprising at least two components at least one of which is a perhydrophenanthrene derivative of claim 1.

14. A dielectric of claim 13, wherein the amount of phenanthrene compound is 0.1 to 60 percent by weight.

15. An electro-optical display element based on a liquid-crystal cell containing a liquid-crystalline dielectric, the improvement wherein the liquid-crystalline dielectric is that of claim 13.

* * * * *